(12) United States Patent
Ogura et al.

(10) Patent No.: US 7,491,408 B2
(45) Date of Patent: Feb. 17, 2009

(54) POLYMER, BIOABSORBABLE MATERIAL AND FILM FOR PREVENTING TISSUE FUSION

(75) Inventors: Atsuhiko Ogura, Tsuchiura (JP); Shinji Tanaka, Tsukuba (JP); Yoshikazu Nakashima, Aichi (JP); Shigeru Kitano, Kawasaki (JP)

(73) Assignee: NOF Corporation, Tokyo (JP)

( * ) Notice: Subject to any disclaimer, the term of this patent is extended or adjusted under 35 U.S.C. 154(b) by 501 days.

(21) Appl. No.: 10/538,799

(22) PCT Filed: Dec. 13, 2002

(86) PCT No.: PCT/JP02/13063

§ 371 (c)(1),
(2), (4) Date: Mar. 28, 2006

(87) PCT Pub. No.: WO2004/055095

PCT Pub. Date: Jul. 1, 2004

(65) Prior Publication Data

US 2006/0252908 A1 Nov. 9, 2006

(51) Int. Cl.
*A61L 15/16* (2006.01)
*A61F 13/00* (2006.01)
*C08G 69/10* (2006.01)

(52) U.S. Cl. .................. 424/444; 424/422; 424/423; 424/426; 424/443; 528/271; 528/310; 528/328; 528/422; 528/425

(58) Field of Classification Search .......... 528/271, 528/310, 328, 422, 428; 424/422, 423, 426, 424/443, 444
See application file for complete search history.

(56) References Cited

U.S. PATENT DOCUMENTS

| 5,225,532 A | * | 7/1993 | Quentin et al. | 530/331 |
| 6,673,361 B1 | * | 1/2004 | Ogura et al. | 424/423 |
| 2001/0009662 A1 | * | 7/2001 | Cohn et al. | 424/78.17 |

FOREIGN PATENT DOCUMENTS

| DE | 195 42 837 | 5/1997 |
| JP | 2002-371131 | 12/2002 |
| WO | WO 00/71601 A1 | * 11/2000 |

OTHER PUBLICATIONS

Shinji Tanaka et al., "Polyethylene Glycol Middle Segment to suru Triblock Kyojugotai no Gosei to Bussei", Polymer Preprints, Japan, vol. 51, No. 10, The Society of Polymer Science, Japan 2002, pp. 2515-2516.

* cited by examiner

*Primary Examiner*—Michael J Feely
(74) *Attorney, Agent, or Firm*—Darby & Darby PC (57) ABSTRACT

A novel $A^1$-B-$A^2$ polymer having a number average molecular weight of 10000 to 100000 is provided that has excellent bioabsorbability so as to disappear in a predetermined period of time even when embedded in a large amount in the body, has good kinetic properties, and is useful for preparing tissue anti-adhesion films. This polymer is composed of segments $A^1$ and $A^2$ each having at least either of modified and unmodified amino acid groups, and segment B composed of PEG having a number average molecular weight of 8000 to 50000. The polymer contains both the modified and unmodified amino acid groups, the content of the modified amino acids is 20 to 85 mol % of all the amino acids in the polymer, and segment $A^1$ is bonded to one end of segment B and segment $A^2$ is bonded to the other end of segment B.

8 Claims, 3 Drawing Sheets

POLYMER, BIOABSORBABLE MATERIAL AND FILM FOR PREVENTING TISSUE FUSION

FIELD OF ART

The present invention relates to novel $A^1$-B-$A^2$ polymers having bioabsorbability, bioabsorbable materials prepared from the polymers, and tissue anti-adhesion films prepared from the bioabsorbable materials which have good mechanical strength and flexibility in a dry state, quickly absorb moisture to form hydrogel when embedded in a living organism, and are degradable and absorbable in a certain period of time even when embedded in a large amount in a living organism.

BACKGROUND ART

High polymer materials used as biomaterials are required to have functions suitable for their applications, such as non-exothermicity, non-toxicity including non-allergenicity, mechanical strength for adapting to tissues and living organisms, ability to separate substances, and ability to release drugs in a sustained manner.

For example, anti-adhesion films used for preventing postoperative tissue adhesion are required to have good adaptability, non-adhesiveness, and low irritativeness to tissues, quick bioabsorbability for dispensing with postoperative removal, and excellent mechanical strength and flexibility in a dry state, which affect the handling property of the films.

Conventional biomaterials, however, are not sufficiently balanced in required functionalities or the like, so that development of materials is desired that fulfill the above requirements in a balanced manner.

A-B-A triblock copolymers are conventionally known, wherein segment B is polyethylene glycol, and segments A on both ends of segment B are modified amino acid groups, such as poly-β-benzyl-L-aspartate (abbreviated as PBLA hereinbelow) or poly-γ-benzyl-L-glutamate (abbreviated as PBLG hereinbelow) (WO00/771602). Such polymers have good kinetic properties, but have a relatively slow biodegradation rate. Thus, when embedded in a large amount in the body, the polymers may not disappear completely in a short period of time, though rarely.

On the other hand, as bioabsorbable materials, there are known hyaluronic acid, collagen, carboxymethyl cellulose, polycaprolactone, regenerated cellulose, polylactic acid, polyglycolic acid, and copolymers of these. However, none of these materials may easily be given an ideal bioabsorption rate or have sufficient mechanical strength and flexibility.

SUMMARY OF THE INVENTION

It is therefore an object of the present invention to provide a novel $A^1$-B-$B^2$ polymer that is capable of disappearing in a predetermined period of time even when embedded in a large amount in the body, and a bioabsorbable material prepared from the polymer.

It is another object of the present invention to provide a bioabsorbable material and a tissue anti-adhesion film that have good kinetic properties in a dry state and excellent bioabsorbability.

According to the present invention, there is provided an $A^1$-B-$A^2$ polymer consisting of segments $A^1$ and $A^2$ each comprising at least either of a modified amino acid group whose functional group is protected with a protective group and an unmodified amino acid group whose functional group is not protected with a protective group, and segment B consisting of polyethylene glycol having a number average molecular weight of 8000 to 50000, with segment $A^1$ binding to one end of segment B and segment $A^2$ binding to the other end of segment B, wherein said polymer comprises both the modified and unmodified amino acid groups, and the content of the modified amino acids is 20 to 85 mol % of all the amino acids in the polymer, and wherein said polymer has a number average molecular weight of 10000 to 100000.

According to the present invention, there is also provided a bioabsorbable material comprising the $A^1$-B-$A^2$ polymer.

According to the present invention, there is further provided a tissue anti-adhesion film obtained by forming the bioabsorbable material into a film.

PREFERRED EMBODIMENTS OF THE INVENTION

The present invention will now be explained in detail.

The $A^1$-B-$A^2$ polymer according to the present invention is a block polymer having a number average molecular weight of 10000 to 100000, wherein segments $A^1$ and $A^2$ having particular amino acid groups are bonded on either ends of segment B consisting of polyethylene glycol (abbreviated as PEG hereinbelow) having a particular molecular weight.

If the number average molecular weight of the polymer is outside the above range, a bioabsorbable formed product prepared from the polymer is not given sufficient kinetic properties and non-irritativeness.

Each of segments $A^1$ and $A^2$ mentioned above has at least either of the modified and unmodified amino acid groups, and the $A^1$-B-$A^2$ polymer of the present invention contains both the modified and unmodified amino acid groups. The content of the modified amino acids as a water-insoluble segment is 20 to 85 mol %, preferably 30 to 85 mol %, more preferably 35 to 80 mol %, of the total amino acids in the polymer.

That is, in the present polymer having both the modified and unmodified amino acid groups, when one of segments $A^1$ and $A^2$ is composed only of the modified amino acid groups, the other necessarily contains the unmodified amino acid groups; when one of segments $A^1$ and $A^2$ is composed only of the unmodified amino acid groups, the other necessarily contains the modified amino acid groups; and when one of segments $A^1$ and $A^2$ is composed of both the modified and unmodified amino acid groups, the other is composed only of the modified amino acid groups, only of the unmodified amino acid groups, or of both the modified and unmodified amino acid groups. It is preferred that each of segments $A^1$ and $A^2$ is composed of both the modified and unmodified amino acid groups for facilitating adjustment of the bioabsorption rate of the formed products, such as films, prepared from the polymer. The modified and/or unmodified amino acid groups in segments $A^1$ and $A^2$ may be the same or different, and the molecular weights of segments $A^1$ and $A^2$ may be the same or different.

If the content of the modified amino acids is less than 20 mol % of all the amino acids in the polymer of the present invention, the tissue adhesion property of the tissue antiadhesion film prepared from the polymer is remarkably deteriorated, whereas if the content is more than 85 mol %, the ability to prevent tissue adhesion is deteriorated and the bioabsorbability is also remarkably lowered. In addition, at the content outside the above-mentioned rage, an ideal bioabsorption rate cannot be achieved easily. The ideal bioabsorption rate may vary depending on the shape and application of the formed product prepared from the polymer, but is such that the formed product is absorbed in the living body and disappears in usually 2 days to 1 week, preferably 3 to 6 days, more preferably 4 to 6 days. In particular, when the formed product is a tissue anti-adhesion film, the film is desirably absorbed and disappears in the living body in 3 to 6 days, more preferably 4 to 6 days.

The modified and/or unmodified amino acid groups contained in segments $A^1$ and $A^2$ may be prepared from raw material amino acids that are polymerizable and capable of being made into modified amino acid-N-carboxylic anhydride (abbreviated as NCA hereinbelow) by the phosgene process. Specific examples of such a raw material amino acid include aspartic acid, glutamic acid, serine, threonine, tyrosine, cysteine, lysine, histidine, and arginine. Among these, aspartic acid and glutamic acid are particularly preferred since these amino acids have a carboxyl group in the side chain, and may be made hydrophobic by esterification with aliphatic or aromatic alcohol, i.e. may easily be made into a modified amino acid. The ester bond given to the amino acid may easily be cleaved in the living body.

The modified amino acid group contained in at least either of the segments $A^1$ and $A^2$ is an amino acid group whose functional group, such as a carboxyl, amino, hydroxyl, or thiol group, is protected with a protective group during synthesis of NCA by the phosgene process. On the other hand, the unmodified amino acid group as used herein means an amino acid group whose functional group is not protected with a protective group, or an amino acid group wherein a metal or the like is bonded to its functional group in its side chain to form a salt.

For forming the modified amino acid group, when the functional group to be protected is a carboxyl group, the protective group therefor maybe, for example, methyl, ethyl, propyl, isopropyl, n-butyl, s-butyl, or t-butyl group, or a straight or branched aliphatic group having 5 to 18 carbon atoms, an alicyclic group having 5 to 18 carbon atoms, or an aromatic group, such as a benzyl group.

When the functional group to be protected is an amino or hydroxyl group, the protective group therefor may be, for example, a group derived from carboxylic acid for amidification or esterification, such as acetyl or propionyl group, a group derived from a straight or branched aliphatic carboxylic acid having 4 to 18 carbon atoms or an alicyclic carboxylic acid having 4 to 18 carbon atoms, or a group derived from aromatic carboxylic acid. Examples of the protective group containing an aromatic group may include benzyloxycarbonyl, benzyl, or o-nitrophenylsulfenyl group.

When the functional group to be protected is a thiol group, the protective group therefor may be, for example, a benzyl group.

The protective group in the modified amino acid group is not limited to the above specific examples, and may be any group as long as it can protect the functional group of an amino acid group to make the amino acid hydrophobic, and can be easily cleaved in the living organism.

Typical examples of the amino acid constituting the modified or unmodified amino acid group may include γ-benzyl-glutamate represented by the formula (1) (abbreviated as BLG hereinbelow), glutamic acid represented by the formula (2) (abbreviated as Glu hereinbelow), sodium glutamate represented by the formula (3) (abbreviated as Glu.Na hereinbelow), β-benzyl aspartate represented by the formula (4) (abbreviated as BLA hereinbelow), aspartic acid represented by the formula (5) (abbreviated as Asp hereinbelow), and sodium aspartate represented by the formula (6) (abbreviated as Asp.Na hereinbelow).

(1)

(2)

(3)

(4)

(5)

(6)

Each of segments $A^1$ and $A^2$ may usually be composed of polyamino acid having one or more units of modified amino acid and/or one or more units of unmodified amino acid. The total number average molecular weight of the polyamino acids composing segments $A^1$ and $A^2$ is usually 20 to 70%, preferably 25 to 65%, more preferably 30 to 60% of the number average molecular weight of the $A^1$-B-$A^2$ polymer of the present invention. If the total number average molecular weight of the polyamino acids is less than 20% of that of the present polymer, sufficient mechanical strength cannot be given to the film prepared from the polymer, whereas at more than 70%, an ideal bioabsorption rate cannot be achieved easily, and the film is not given flexibility.

The total number average molecular weight of the polyamino acids composing segments $A^1$ and $A^2$ is usually 2000 to 70000, preferably 3000 to 60000, more preferably 4000 to 40000, most preferably 6000 to 14000, for giving good kinetic properties to the film prepared from the polymer. The number average molecular weight of the polyamino acid composing each segment $A^1$ or $A^2$ is usually 1000 to 35000, preferably 1500 to 30000, more preferably 2000 to 20000, most preferably 3000 to 7000.

In the polymer of the present invention, the water-soluble PEG composing segment B may have amino groups at both ends, such as aminomethyl, aminoethyl, or aminopropyl group.

The number average molecular weight of segment B needs to be 8000 to 50000, preferably 10000 to 30000, more preferably 11000 to 20000, for facilitating balancing between a good bioabsorption rate and kinetic properties in the film prepared from the present polymer. At a number average molecular weight of less than 8000, sufficient properties are hardly given, whereas at a number average molecular weight of more than 50000, the viscosity of PEG as a raw material of the polymer is too high to produce the polymer conveniently.

The polymer of the present invention may be any polymer as long as segment $A^1$ is bonded to one end of segment B and segment $A^2$ is bonded to the other end of segment B, and segments $A^1$ and $A^2$ may be bonded via any bond at the ends of segment B. When the polymer of the present invention is to be used in the field where low irritativeness to the living organism is required, polymers represented by the formula (7), for example, may preferably be used.

(7)

In the formula (7), R's may be the same or different and each stands for $-CH_2COONa$, $-CH_2COOH$, or $-CH_2COOC_6H_5$. a and d denote the number of repeat units in segments $A^1$ and $A^2$, respectively, and is an integer of 1 or more, preferably 5 to 100. b represents the number of methylene groups repeated in the bond between segments B and $A^1$ or B and $A^2$, and is an integer of preferably 1 to 10. c represents the number of oxyethylene groups repeated, and is an integer of preferably 200 to 1200. Preferred embodiments of the present polymer include one or a mixture of two or more polymers represented by the formula (7). Incidentally, a, b, c, and d in the formula (7) denoting the numbers of repeat merely represent rough numbers calculated from the number average molecular weights mentioned above, and thus are not limited to the above ranges.

The polymer of the present invention may readily be prepared, for example, by a method including the steps of:

(X) reacting NCA with PEG constituting segment B having primary amino groups at both ends, by ring opening addition polymerization to prepare an A-B-A polymer wherein segments A composed of modified or poly modified amino acids are bonded at both ends of segment B, and (Y) decomposing and removing a modifying group of some of the modified amino acid units constituting segments A by hydrolysis with alkali, catalytic hydrogenation, enzymolysis, or the like reaction of the A-B-A polymer.

In preparing the polymer, the number average molecular weight of each segment may easily be controlled by adjusting the molecular weight of PEG and the amount of NCA added in step (X), and the amount of the modifying groups to be decomposed and removed from segments A in step (Y).

In step (X), the A-B-A polymer may be prepared, using PEG of a desired number average molecular weight having primary amino groups at both ends, which may be a commercially available product, and by mixing with PEG a desired NCA prepared by a conventional method or the like, and reacting the mixture by conventional ring opening addition polymerization usually at 20 to 50° C. for 6 to 36 hours. In the polymerization reaction, solvents, such as N,N-dimethylformamide (abbreviated as DMF hereinbelow), dimethyl sulfoxide, N,N-dimethylacetamide, or 1,4-dioxane, or a mixture of these solvents with dichloromethane or chloroform, may be used.

In step (Y), the modifying group of some of the modified amino acid units consisting segment A may be decomposed and removed by, for example, hydrolysis with alkali usually at 0 to 60° C. for 0.1 to 1 hour, wherein the amount of alkali is adjusted so that the resulting polymer contains the amount of modified amino acids as in the present polymer. The hydrolysis with alkali may be replaced with catalytic hydrogenation or enzymolysis, wherein the conditions, kind and amount of enzymes, or the like parameters may suitably be selected so that the resulting polymer contains the amount of modified amino acids as in the present polymer.

The $A^1$-B-$A^2$ polymer of the present invention has moisture retaining ability, hydrogel forming property, bioabsorbability, and the like properties. Thus the present polymer may be used as a raw material for bioabsorbable materials and tissue anti-adhesion films to be discussed later, and also finds applications in a raw material for various products such as toiletry products or various cosmetics.

The bioabsorbable material of the present invention contains the $A^1$-B-$A^2$ polymer of the present invention, and fulfills kinetic properties and non-irritativeness required when the product formed of the material is to be embedded in the living organism.

The bioabsorbable material of the present invention may optionally contain, in addition to the polymer of the present invention, other bioabsorbable polymers such as known polymers having bioabsorbability, as desired. Examples of such other bioabsorbable polymers may include PBLA-PEG-PBLA triblock copolymers, PBLG-PEG-PBLG triblock copolymers, hyaluronic acid, collagen, carboxymethyl cellulose, polycaprolactone, polylactic acid, polyglycolic acid, and copolymers thereof.

The content of the other bioabsorbable polymer may suitably be selected so that the formed product prepared from the present bioabsorbable material has a desired bioabsorption rate and mechanical strength, and is preferably 0 to 50 wt %.

The bioabsorbable material of the present invention may easily be made into a sheet-like formed product by, for example, casting or hot pressing, but the shape of the formed product is not particularly limited. The resulting formed product usually has good mechanical strength and rubber elasticity in a dry state.

When the bioabsorbable material of the present invention is made into a formed product in the form of a sheet or the like, the bioabsorption rate of the formed product may easily be controlled by adjusting the number average molecular weights and molecular weight ratio of segments B, $A^1$, and $A^2$ of the $A^1$-B-$A^2$ polymer of the present invention contained in the present bioabsorbable material, the shape and thickness of the formed product, the molar ratio of the unmodified and modified amino acids in the polymer, or the like parameters.

The tissue anti-adhesion film of the present invention is a product obtained by forming the bioabsorbable material of the present invention into a sheet, film, or the like form. The thickness of the film is not particularly limited, and may suitably be selected from the range of, for example, 0.1 to 2 mm, depending on the location to which the film is to be applied, or the like factors.

The tissue anti-adhesion film of the present invention may be prepared by forming the bioabsorbable material of the present invention into a film, for example, by conventional casting or heat pressing. Alternatively, the present anti-adhesion film may also be prepared by first preparing an A-B-A polymer wherein segments A composed of modified or poly modified amino acid are bonded at both ends of segment B in accordance with step (X) of the method for producing the polymer of the present invention discussed above, optionally mixing the A-B-A polymer with the other bioabsorbable polymers mentioned above or the present polymer to prepare a polymer material, forming the polymer material into a film according to a method such as the conventional method mentioned above, and then subjecting the resulting film to hydrolysis with alkali, catalytic hydrogenation, enzymolysis, or the like reaction to decompose and remove the modifying group of some of the modified amino acid units constituting segments A in the film according to step (Y) discussed above.

For achieving the ideal bioabsorption rate, the content of the modified amino acids in the tissue anti-adhesion film of the present invention is preferably 20 to 85 mol %, more preferably 30 to 85 mol %, most preferably 35 to 80 mol % of the total amino acids in the film. Further, it is desirable that the present anti-adhesion film is composed essentially of the polymer of the present invention.

The tissue anti-adhesion film of the present invention, when placed in water, forms hydrogel. This hydrogel has sufficient flexibility, and is capable of maintaining its original swollen shape even when left in the swollen state in water at room temperature for a prolonged time. Thus the tissue anti-adhesion film of the present invention exhibits excellent handling property in placing the film on the tissues of animals including human, and excellent shape adaptability to soft tissues when gelled.

EXAMPLES

The present invention will now be explained in more detail with reference to Examples, which are illustrative only and do not intend to limit the present invention. The following is the methods of analysis and its conditions employed in the Examples.

<Measurement (1) of $^1$H-NMR>
Model: JNM EX270 manufactured by JEOL LTD.; Solvent: $D_2O$ (containing 0.5 N NaOH); Internal Standard: $H_2O$ (4.70 ppm)

<Measurement (2) of $^1$H-NMR>
Model: JNM EX270 manufactured by JEOL LTD.; Solvent DMSO-$d_6$;
Temperature: 80° C.; Internal Standard: DMSO (2.62 ppm)

<Preparation (1) of Bioabsorbable Sheet>
500 mg of a polymer is held between metal plates previously heated to 100° C. to soften for 3 minutes, and a load of 10 MPa is applied for 3 minutes. After cooling, the film is peeled off to obtain a colorless, translucent sheet. All the sheets prepared from the polymers obtained in the Examples of the present invention, when introduced into water, gradually swollen and formed colorless, transparent hydrogel.

<Preparation (2) of Bioabsorbable Sheet>
500 mg of a polymer is dissolved completely in 5 ml of methylene chloride. The resulting polymer solution is cast in a petri dish made of polytetrafluoroethylene, and the solvent is evaporated at room temperature for 1 hour. Then the petri dish is dried in a high temperature phase set at 60° C. for 1 hour to thereby obtain a colorless, translucent sheet.

<Bioabsorbability Test>
The bioabsorbability test is conducted by embedding a sample sheet in 2 cm square in the abdominal cavity of eight-week-old male ddy mice by abdominal operation. When it is confirmed that the sheet absorbs the body fluid on the tissue surface to adhere to the tissue, and is rapidly softened and adapted to the soft tissues therearound, then the peritoneum is sutured. The mice having the sheet embedded are raised for three days from the next day, and three of them are slaughtered per day, and the embedded sheets are taken out by abdominal operation to measure the dry weight. The difference between the value obtained by this measurement and the sheet weight before the embedment is taken as the test result.

<Test on Ability to Prevent Adhesion>
The test on ability to prevent adhesion is conducted by ligating the base of the iliac vein of a seven-week-old female Wistar rat with 3-0 silk thread for blood stanching, and cutting the vein at about 1 mm down stream of the ligation. A sample sheet is applied over the treatment site, and the peritoneum and skin are sutured. One week after, adhesion in the living tissues is evaluated by abdominal operation. The antiadhesion ratio is calculated in accordance with the following formula:

Antiadhesion ratio (%)=(no adhesion/total number (=adhesion observed+no adhesion ))×100

<Tensile Test>
A sheet is measured for thickness, and cut into strips of about 2 mm wide. Each sample was measured for the tensile strength ten times, and the average of eight measurements is taken as the result. The maximum load is obtained by dividing the average of the eight measurements with the cross sectional area.

Example 1

[Synthesis of Polymer]

1.0 g of PEG having amino groups at both ends (20000 g/mol) was dissolved in 7 ml of DMF in a 40° C. oil bath in a dry inert gas atmosphere, and 800 mg (64 equivalents of PEG) of β-benzyl-L-aspartate-N-carboxylic anhydride (abbreviated as BLA-NCA hereinbelow) was added. After overnight reaction, the reactant was added dropwise into an ice-cooled diisopropyl ether to precipitate white solid. The solid was separated by suction filtration, dissolved in methylene chloride, crystallized repeatedly, and dried under reduced pressure, to thereby obtain a PBLA-PEG-PBLA block copolymer.

1.0 g of the obtained block copolymer was re-dissolved in 10 ml of chloroform, and 0.78 ml of a 0.43N sodium hydroxide solution was added. After reacting for 10 minutes at room temperature, the reactant was added dropwise into diisopropyl ether to precipitate white solid. The solid was separated by suction filtration, and dried under reduced pressure to thereby obtain PEG-P(BLA,Asp.Na,Asp) polymer of the $A^1$-B-$A^2$ type.

Various number average molecular weights as shown in Table 1 of the obtained polymer were measured by GPC. The results are shown in Table 1.

[Measurement of $^1$H-NMR]

According to Measurement (1) of $^1$H-NMR mentioned above, $^1$H-NMR of the obtained PBLA-PEG-PBLA block copolymer and PEG-P(BLA,Asp.Na,Asp) polymer was measured. The bonded BLA content was calculated from the amounts of bonded BLA in the two polymers in accordance with the following formula. The bonded BLA content was calculated using the peak areas at 3.6 ppm and 7.3 ppm of $^1$H-NMR.

BLA Content (%)=[Amount of bonded BLA in PEG-P(BLA,Asp.Na,Asp)polymer/Amount of bonded BLA in $A^1$-B-$A^2$ block copolymer]×100

Figure 1:
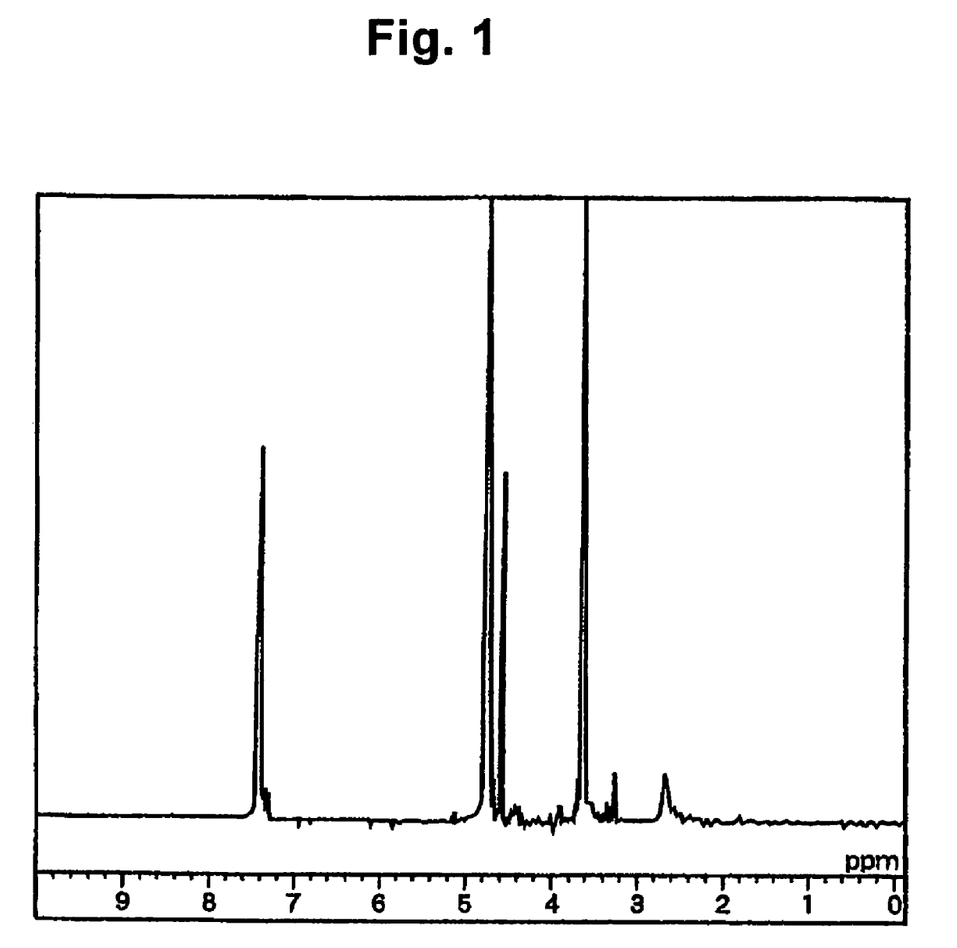
FIG. 1 is a $^1$H-NMR spectrum of the polymer synthesized in Example 1 according to the present invention.

The BLA content with respect to the total amino acids in the obtained polymer is shown in Table 1. The $^1$H-NMR spectrum of PEG-P(BLA,Asp.Na,Asp)polymer is shown in FIG. 1.

[Preparation of Biodegradable Sheet and Biodegradability Test]

A bioabsorbable sheet was prepared using the thus synthesized PEG-P(BLA,Asp.Na,Asp) polymer in accordance with Preparation (1) of Bioabsorbable Sheet discussed above.

The obtained PEG-P(BLA,Asp.Na,Asp) polymer sheet was embedded in the abdominal cavity of an eight-week-old male ddy mouse by abdominal operation in accordance with the Bioabsorbability Test discussed above, and the postoperative residual amount of the sheet was measured. The results are shown in FIG. 2.

Figure 2:
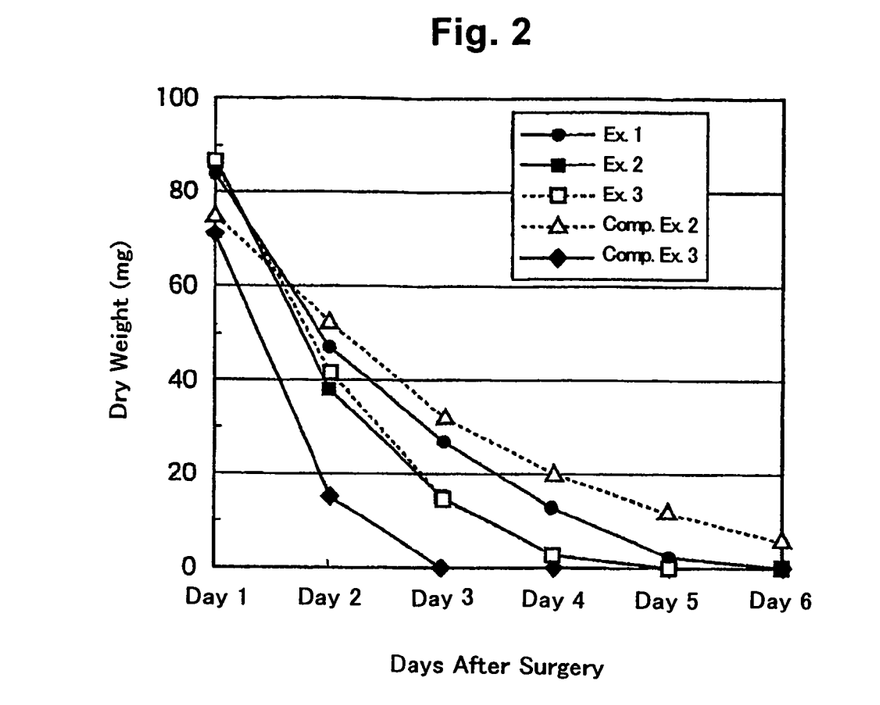
FIG. 2 is a graph showing the results of measurement of biodegradability in the abdominal cavity of mice of the polymers prepared in Examples 1 and 2 and Comparative Examples 2 and 3.

From FIG. 2, it is seen that the sheet did not disappear completely at three days after the sheet embedment, but completely disappeared at six days after the embedment. In view of the time required for tissue restoration at the abdominal section, where the wound was not restored sufficiently in 3 days, but was believed to be restored sufficiently in about a week, the sheet showed an ideal result.

[Test on Ability to Prevent Adhesion]

The test on ability of the sheet prepared above to prevent adhesion was conducted on the number of rats shown in Table 1 in accordance with the procedures discussed in Test on Ability to Prevent Adhesion above. The results are shown in Table 1.

[Tensile Test]

Figure 3:
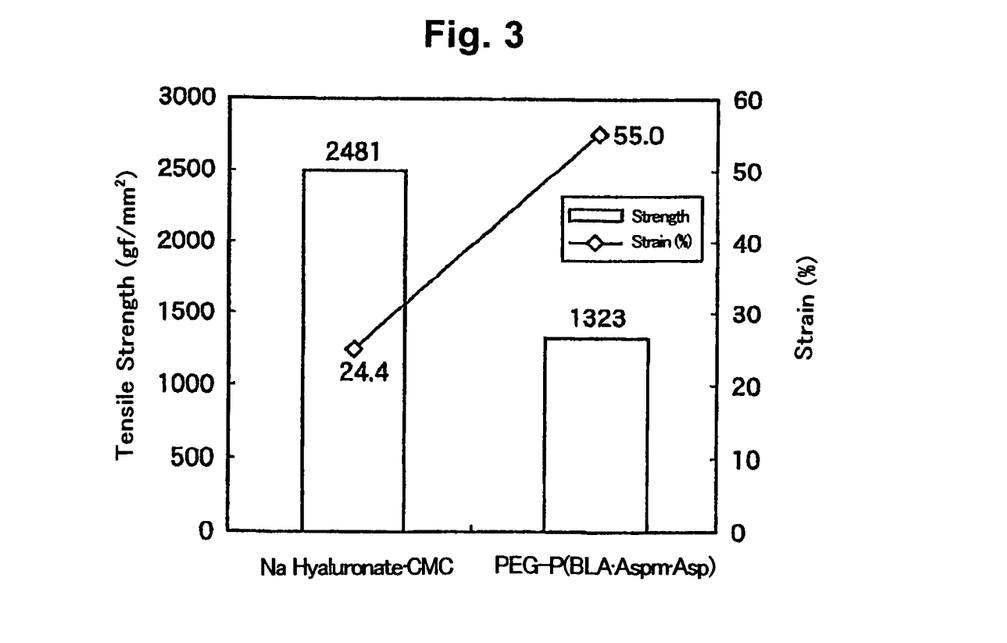
FIG. 3 is a graph showing the results of measurements of tensile strengths of the tissue anti-adhesion film prepared from the polymer of the present invention synthesized in Example 1 and of a commercial tissue anti-adhesion film.
Figure 4:
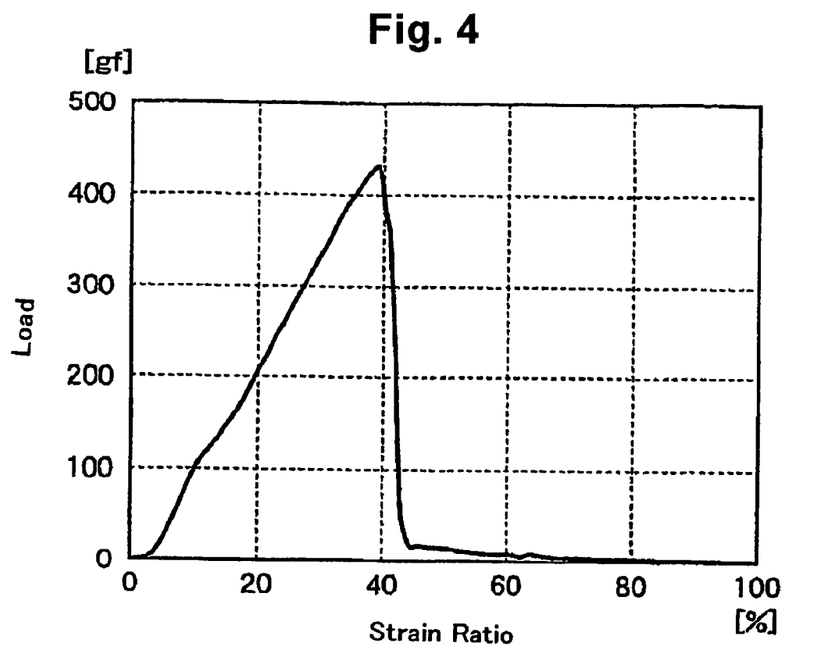
FIG. 4 illustrates the stress-strain curve obtained in a tensile strength test on the tissue anti-adhesion film prepared from the polymer synthesized in Example 1 according to the present invention.
Figure 5:
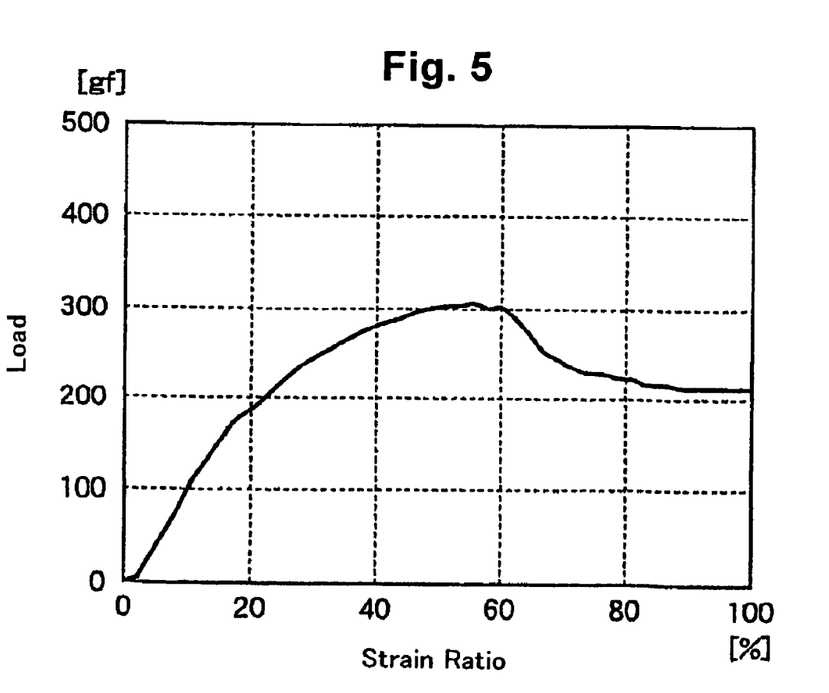
FIG. 5 illustrates the stress-strain curve obtained in a tensile strength test on a commercial tissue anti-adhesion film.

The sheet prepared above was subjected to a tensile test in accordance with the procedures discussed in Tensile Test above. The same test was also conducted on a synthetic absorbable anti-adhesion sheet containing sodium hyaluronate and carboxymethyl cellulose at 2:1 (molar ratio) (abbreviated as Na hyaluronate.CMC hereinbelow), which was commercially available from Genzyme Corporation. The results are shown in FIG. 3. Further, the stress-strain curve of the sheet of this example is shown in FIG. 4, and that of the commercial Na hyaluronate CMC is shown in FIG. 5.

From FIG. 3, it is seen that the obtained sheet had high strain capacity and was ductile, though the tensile strength was inferior. From FIGS. 4 and 5, it is seen that the sheet of the present example was not broken after the yield point but deformed plastically. Thus it is understood that the sheet of the present example had better handling property than the commercial sheet.

Example 2

PBLA-PEG-PBLA block polymer and PEG-P(BLA,Asp.Na,Asp) polymer of the $A^1$-B-$A^2$ type were prepared in the same way as in Example 1, except that the PEG was replaced with PEG having amino groups at both ends (11000 g/mol), and the amount of the sodium hydroxide solution was 1.86 ml.

Using the obtained polymers, various number average molecular weights and $^1$H-NMR were measured, the BLA content was calculated, and the bioabsorbable sheet was prepared and subjected to the tests in the same way as in Example 1. The results of the bioabsorbability test are shown in FIG. 2, and the number average molecular weights, the BLA content, and the results of the test on ability to prevent adhesion are shown in Table 1.

Example 3

PBLA-PEG-PBLA block polymer and PEG-P(BLA,Asp.Na,Asp) polymer of the $A^1$-B-$A^2$ type were prepared in the same way as in Example 1, except that the amount of BLA-NCA was 100 equivalents of PEG, and the amount of the sodium hydroxide solution was 1.80 ml.

Using the obtained polymers, various number average molecular weights and $^1$H-NMR were measured, the BLA content was calculated, and the bioabsorbable sheet was prepared and subjected to the tests in the same way as in Example 1. The results of the bioabsorbability test are shown in FIG. 2, and the number average molecular weights, the BLA content, and the results of the test on ability to prevent adhesion are shown in Table 1.

Example 4

PBLG-PEG-PBLG block polymer and PEG-P(BLG,Glu.Na,Glu) polymer of the $A^1$-B-$A^2$ type were prepared in the same way as in Example 1, except that BLA-NCA was replaced with γ-benzyl-L-glutamate-N-carboxylic anhydride (abbreviated as BLG-NCA hereinbelow).

Using the obtained polymers, various number average molecular weights and $^1$H-NMR were measured, the BLG content was calculated, and the biodegradable sheet was prepared and subjected to the tests in the same way as in Example 1. The results of the biodegradability test are shown in FIG. 2, and the number average molecular weights, the BLG content, and the results of the test on ability to prevent adhesion are shown in Table 1.

COMPARATIVE EXAMPLE 1

The test on ability to prevent adhesion was conducted without an anti-adhesion film. The results are shown in Table 1.

COMPARATIVE EXAMPLE 2

A bioabsorbable sheet was prepared with the PBLA-PEG-PBLA block polymer synthesized in Example 1. The number average molecular weights were measured, the BLA content was calculated, and the test on ability to prevent adhesion was conducted in the same way as in Example 1. The results are shown in Table 1. The bioabsorbability test was also conducted in the same way as in Example 1. The results are shown in FIG. 2.

COMPARATIVE EXAMPLE 3

PBLA-PEG-PBLA block copolymer was prepared in the same way as in Example 1, except that the PEG was replaced with PEG having amino groups at both ends (4000 g/mol) and the amount of BLA-NCA was 1.74 g (28 equivalents of PEG).

A bioabsorbable sheet was prepared with the obtained block copolymer. The number average molecular weights were measured, the BLA content was calculated, and the test on ability to prevent adhesion was conducted in the same way as in Example 1. The results are shown in Table 1. Further, the bioabsorbability test was conducted in the same way as in Example 1. The results are shown in FIG. 2.

COMPARATIVE EXAMPLE 4

PBLA-PEG-PBLA block polymer and PEG-P(BLA,Asp.Na,Asp) polymer of the $A^1$-B-$A^2$ type were prepared in the same way as in Example 1, except that the PEG was replaced with PEG having amino groups at both ends (11000 g/mol), and the amount of the sodium hydroxide solution was 3.34 ml.

A bioabsorbable sheet was prepared from the obtained PEG-P(BLA,Asp.Na,Asp) polymer in the same way as in Example 1. The number average molecular weights were measured, the BLA content was calculated, and the test on ability to prevent adhesion was conducted in the same way as in Example 1. The results are shown in Table 1.

COMPARATIVE EXAMPLE 5

PBLA-PEG-PBLA block polymer and PEG-P(BLA,Asp.Na,Asp) polymer of the $A^1$-B-$A^2$ type were prepared in the same way as in Example 1, except that the amount of the sodium hydroxide solution was 0.26 ml.

A bioabsorbable sheet was prepared from the obtained PEG-P(BLA,Asp.Na,Asp) polymer in the same way as in Example 1. The number average molecular weights were measured, the BLA content was calculated, and the test on ability to prevent adhesion was conducted in the same way as in Example 1. The results are shown in Table 1.

COMPARATIVE EXAMPLE 6

The test on ability to prevent adhesion was conducted on the commercially available Na hyaluronate.CMC in the same way as in Example 1. The results are shown in Table 1.

TABLE 1

| | | Example 1 | Example 2 | Example 3 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|---|---|
| Component | Number average molecular weight of PEG | 20000 | 11000 | 20000 | — | 20000 | 4000 | 11000 | 20000 | — |
| | Number average molecular weight of amino acids | 8500 | 7500 | 7500 | — | 10000 | 2000 | 5500 | 9500 | — |
| | Number average molecular weight of polymer | 28500 | 27500 | 27500 | — | 30000 | 6000 | 16500 | 29500 | — |
| | Content of modified amino acids (mol %) | 70 | 50 | 50 | — | 100 | 100 | 10 | 90 | — |
| Test on ability to prevent adhesion | Adhesion observed (animals) | 4 | 5 | 4 | 9 | 16 | 14 | 14 | 13 | 12 |
| | Adhesion not observed (animals) | 16 | 15 | 15 | 1 | 3 | 5 | 4 | 5 | 6 |
| | Number tested (animals) | 20 | 20 | 19 | 10 | 19 | 19 | 18 | 18 | 18 |
| | Antiadhesion Ratio | 80 | 75 | 79 | 10 | 16 | 27 | 22 | 28 | 33 |
| | Residual sheet | Not observed | Not observed | Not observed | — | Observed | Not observed | Not observed | Observed | Not observed |

From the results of the above tests, it was understood that excellent advantages were obtained in the Examples with the polymers of the present invention. That is, even when the tissue anti-adhesion films prepared by forming the bioabsorbable material into sheets, were embedded in a large amount in the abdominal cavity of rats, no rats were found abnormal, and by abdominal operation, the sheets were observed to have disappeared completely after one week and no adhesion was observed at the operation site. On the other hand, it has been reported that PBLA-PEG-PBLA block copolymer sheets as used in Comparative Example 2, when embedded in a large amount in the abdominal cavity of rats, may not disappear completely and remain in the body for a prolonged period of time. In the actual surgery, a plurality of tissue anti-adhesion films are often used at a time. Thus the excellent bioabsorbability achieved in the present invention provides a remarkable advantage.

Further, the commercially available Na hyaluronate.CMC is a hard and brittle material, and thus very likely to be broken upon use. On the other hand, the sheet prepared in Example 1 was not broken even when stretched over 500% in a dry state, providing excellent kinetic properties. When actually placed in the abdominal cavity, the sheet prepared with the polymer of the present invention absorbed the moisture in the abdominal cavity to adhere to the soft tissues, without damaging the tissues or being damaged itself. Thus, it was confirmed that the polymer of the present invention is suitable for biodegradable materials and tissue anti-adhesion films.

What is claimed is:

1. An $A^1$-B-$A^2$ polymer consisting of segments $A^1$ and $A^2$ each comprising at least either of a modified amino acid group whose functional group is protected with a protective group and an unmodified amino acid group whose functional group is not protected with a protective group, and segment B consisting of polyethylene glycol having a number average molecular weight of 8000 to 50000, with segment $A^1$ binding to one end of segment B and segment $A^2$ binding to the other end of segment B, wherein said polymer comprises both the modified and unmodified amino acid groups, and the content of the modified amino acids is 20 to 85 mol % of all the amino acids in the polymer, and wherein said polymer has a number average molecular weight of 10000 to 100000.

2. The $A^1$-B-$A^2$ polymer of claim 1, wherein the total number average molecular weights of segments $A^1$ and $A^2$ is 20 to 70% of the number average molecular weight of the $A^1$-B-$A^2$ polymer.

3. The $A^1$-B-$A^2$ polymer of claim 1, wherein said protective group of the modified amino acid group is selected from the group consisting of methyl, ethyl, propyl, isopropyl, n-butyl, s-butyl, t-butyl, acetyl, propionyl, benzyl, benzyloxycarbonyl, and o-nitrophenylsulfenyl groups, and aliphatic groups having 4 to 18 carbon atoms, and alicyclic groups having 4 to 18 carbon atoms.

4. The $A^1$-B-$A^2$ polymer of claim 1, wherein a raw material amino acid for the modified and unmodified amino acid groups is at least one material selected from the group consisting of L-glutamic acid and L-aspartic acid.

5. The $A^1$-B-$A^2$ polymer of claim 1, wherein the modified amino acid group is selected from the group consisting of β-benzyl-L-aspartate and γ-benzyl-L-glutamate.

6. A bioabsorbable material comprising the $A^1$-B-$A^2$ polymer of claim 1.

7. A tissue anti-adhesion film obtained by forming the bioabsorbable material of claim 6 into a film shape.

8. The tissue anti-adhesion film of claim 7, wherein the content of the modified amino acids is 20 to 85 mol % of all the amino acids in the film.

* * * * *